United States Patent [19]

Peabody

[11] Patent Number: 4,718,890
[45] Date of Patent: Jan. 12, 1988

[54] CONTINUOUS FLOW PERITONEAL DIALYSIS SYSTEM AND METHOD

[76] Inventor: Alan M. Peabody, 102 Meadow Creek Ct., Greer, S.C. 29651

[21] Appl. No.: 840,142

[22] Filed: Mar. 17, 1986

Related U.S. Application Data

[63] Continuation-in-part of Ser. No. 629,130, Jul. 9, 1984, Pat. No. 4,586,920.

[51] Int. Cl.$^4$ ............................................. A61M 5/00
[52] U.S. Cl. ...................................... 604/29; 604/31; 604/65; 128/DIG. 13
[58] Field of Search ................... 604/27–29, 604/31, 65, 67, 81, 131, 375, 411; 124/DIG. 12, DIG. 13; 210/90

[56] References Cited

U.S. PATENT DOCUMENTS

| | | | |
|---|---|---|---|
| 3,545,438 | 12/1970 | DeVries | 604/28 |
| 3,709,222 | 1/1973 | DeVries | 604/29 |
| 3,730,183 | 5/1973 | Goldsmith et al. | 604/29 |
| 4,240,408 | 12/1980 | Schael | 604/28 |
| 4,269,708 | 5/1981 | Bonomini et al. | 210/90 |
| 4,303,068 | 12/1981 | Zelman | 604/29 |
| 4,311,587 | 1/1982 | Nose et al. | 604/29 |
| 4,338,190 | 7/1982 | Kraus et al. | 604/29 |

FOREIGN PATENT DOCUMENTS 2371931 7/1978 France ....................... 604/29

*Primary Examiner*—Stephen C. Pellegrino
*Assistant Examiner*—Jerome R. Smith, Jr.
*Attorney, Agent, or Firm*—Cort Flint

[57] ABSTRACT

A continuous flow peritoneal dialysis system and process is disclosed which includes a source of sterilized peritoneal dialysis system in the form of a gravity feed head vessel (32). A by-pass valve (34) connects the head vessel to an inflow/outflow directional valve 40 which controls the inflow and outflow of the sterilized dialysis fluid to a peritoneal catheter (12). The peritoneal catheter is implanted into the peritoneal membrane (14) of the peritoneal cavity (15). A connectable/disconnectable inflow line (42) and outflow line (48) are connected to an inflow catheter (44) and outflow catheter (46), respectively, of the double peritoneal catheter (12). A pressure monitor (50) in the outflow line (48) monitors the pressure within the cavity (15) and adjusts the inflow and outflow accordingly to maintain a predetermined volume and pressure of dialysis fluid in the cavity to maintain the membrane (14) properly distended at all times for maximum dialysis efficiency and patient comfort. Secondarily, an outflow monitor (54) monitors the outflow and if need be, increases or decreases the inflow to the directional valve (40) by controlling a by-pass valve 34. Control of the level of dialysis fluid in the head vessel (32) is maintained by a level monitor (38) which also can operate the by-pass valve (34) to by-pass fluid to a drain tank (36). Sterile dialysis fluid flows through the cavity (15) in an open single-pass circuit and flows into the disposal and drain tank (36) upon passing through the cavity.

11 Claims, 3 Drawing Figures

CONTINUOUS FLOW PERITONEAL DIALYSIS SYSTEM AND METHOD

CROSS REFERENCED TO RELATED APPLICATION

This application is a continuation-in-part of application Ser. No. 06/629,130 entitled Continuous Flow Peritoneal Dialysis System and Method, filed July 9, 1984, which is now U.S. Pat. No. 4,586,920.

BACKGROUND OF THE INVENTION

The invention relates to a dialysis process for purifying the blood by continuous flow of a dialysate and exchange across the peritoneal membrane.

Heretofore, artificial kidney users have relied basically on two processes for purifying the blood. Hemodialysis involves the circulation of blood through a dialysis machine in which an exchange of the toxic metabolites takes place across an artificial membrane outside of the patient's body. This process requires the assistance of trained personnel and subjects the patient to dangers of mechanical malfunction due to the fact that blood vessels are involved.

Peritoneal dialysis involves the infusion of a sterile dialysate into the peritoneal cavity and after absorbing waste metabolites, the dialysate is discarded. The process is then repeated until the level of metabolytes is reduced to a desired level. This method is commonly referred to as the "Batch" method due to the fact that multiple one or two liter bottles or bags of fresh dialysate solution are utilized which require multiple connections to be made to the catheter inserted in the peritoneal cavity during the dialysis process. The multiple connections made during the course of the dialysis has been thought to be a major cause of the high instance of peritonitis.

Continuous ambulatory peritoneal dialysis offers continuous peritoneal dialysis while still allowing the patient some off time. However, the continuous ambulatory peritoneal dialysis must be done in absence of a machine and multiple bottles or bags of dialysis must be infused daily. Thus, multiple infusions per day requires that multiple connections of bags or bottles to the peritoneal catheter be made. The production of bulk sterile dialysis for the peritoneal process has not been shown to be practical for large scale application particularly for home dialysis.

U.S. Pat. No. 4,311,587 seeks to avoid some of the above problems with peritoneal dialysis by providing a sub-micron filter on line with the fresh dialysate to prevent peritoneal contamination. The system is perambulatory and the bag of dialysate is worn by the patient. The bag may be pressurized by numerous methods and is connected only to the inflow side of the filter. The outflow port of the filter is connected on the other side of the filter so that no peritoneal contaminating source is connected directly to the peritoneal cavity. The system is still basically a batch type system in that multiple bottles or bags of dialysate must be connected to the filter even though direct connection to the peritoneal catheter is not required.

U.S. Pat. No. 4,338,190 discloses a system and process which attempts to avoid the batch process method utilized heretofore in peritoneal dialysis wherein a closed loop peritoneal circuit is provided having a selective membrane across which toxic metabolites are exchanged. A solution is passed on the other side of the selective membrane for maintaining the original concentration of sugar and salt in the peritoneal fluid as the toxic metabolites pass the separator membrane. A double peritoneal catheter provides for the inflow and outflow of the peritoneal fluid. However, the peritoneal fluid is constantly recirculated through the peritoneal cavity and the efficiency becomes reduced slightly because of residual toxins which are put back into the peritoneal cavity. The selective membrane is an expensive disposable item which means that the cost of operating the system is high unless the membrane is re-cleaned. Pumping the peritoneal fluid through the peritoneal cavity is required making it difficult to assure that the patient stays properly distended during the dialysis process. If the peritoneal membrane is not fully distended, it becomes convoluted around the intestines and pockets are formed where the peritoneal fluid can hide. Incomplete circulation then results with decreased efficiency of dialysis. No control is had over the level of the peritoneal fluid in the peritoneal circuit. There is no way of replenishing the peritoneal fluid should the circuit run low on fluid or run dry.

Accordingly, an important object of the present invention is to provide a continuous flow peritoneal dialysis system and method which avoid the inherent problems and dangers of a batch type peritoneal dialysis system.

Still another important object of the present invention is to provide a peritoneal dialysis system having a high rate of dialysate exchange providing increased dialysis efficiency.

Still another important object of the present invention is to provide a peritoneal dialysis system and method having a high rate of dialysate exchange and dialysis efficiency in which the danger of peritoneal infection is minimized.

Still another important object of the present invention is to provide a continuous-flow single-pass peritoneal dialysis system and method in which the pressure and volume of dialysate in the patient's peritoneal membrane is monitored to provide for proper distention of the membrane at all times.

SUMMARY OF THE INVENTION

The above objectives are accomplished according to the present invention by a system and process of peritoneal dialysis in which a continuous flow of sterile dialysis fluid is produced and caused to flow through the peritoneal cavity of the patient in a single-pass open-circuit. The exchange of toxic metabolites occurs across the patient's peritoneal membrane and the residual dialysis solution is drained away after leaving the patient's cavity. A gravity fed system is utilized avoiding the pumping of the fluid through the cavity. A by-pass valve is utilized in combination with a flow monitor to adjust the inflow of sterile dialysis fluid going into the peritoneal cavity and make the inflow equal to the flow coming out of the cavity so that a predetermined volume of fluid in the cavity is maintained at all times. A pressure monitor is utilized to sense the pressure of the fluid in the cavity to make sure that the membrane is not over-distended or under-distended for efficient and comfortable peritoneal dialysis. The pressure monitor controls an inflow/outflow directional valve. If the pressure becomes excessive causing over-distention, the inflow is cut-off or throttled and the outflow is left opened or opened further as need be to control or relieve pressure. If the pressure drops, causing under-distention and convolutions, the directional valve throttles outflow and opens inflow as needed. The continuous flow of peritoneal dialysis fluid provides a high rate of toxic metabolite exchange as the fluid flows in a single pass through the cavity. In this manner, dialysis for six to eight hours approximately three times a week is sufficient for peritoneal dialysis.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
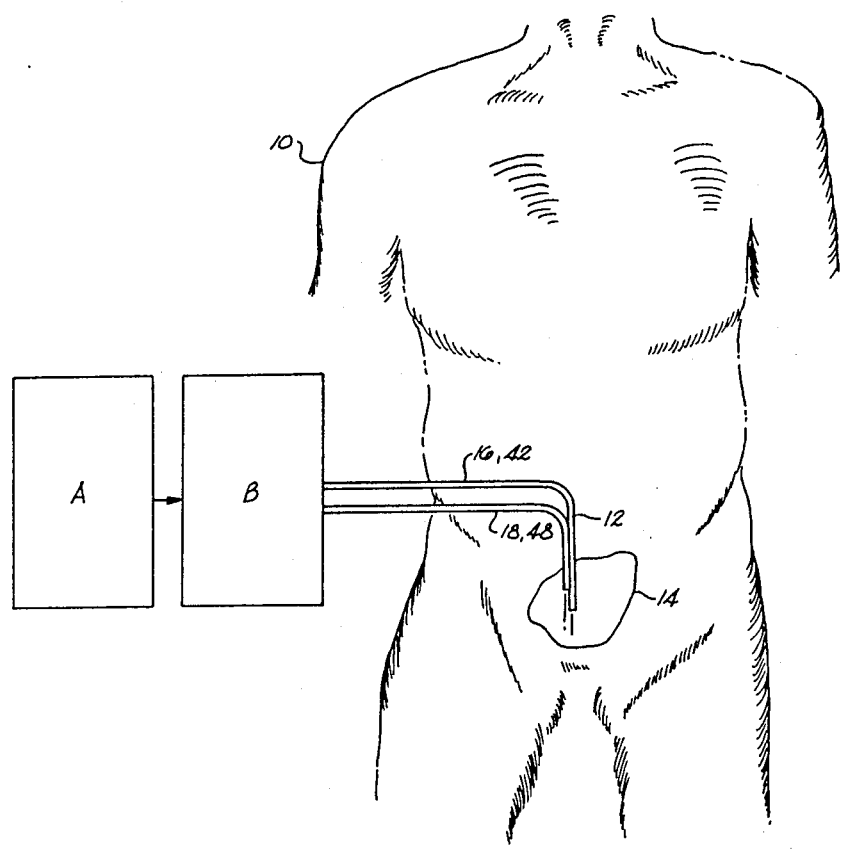
FIG. 1 is a schematic elevation illustrating the continuous flow peritoneal dialysis system and method according to the invention in a patient implant.

The present invention relates to peritoneal dialysis. As is currently practiced, peritoneal dialysis is about one-fifth as efficient as hemodialysis in the removal of solute from the body. Previous studies have demonstrated that the efficiency of peritoneal dialysis can be made to approximate that of hemodialysis if the rate of dialysate exchange is raised to ten liters or more per hour. Presently, the rate of exchange of peritoneal dialysis is approximately two liters every four hours. The invention then is directed to continuously producing moderate quantities of sterile dialysis fluid for peritoneal dialysis and a system and method of passing a continuous-flow of the sterile dialysis fluid through the peritoneal cavity of the patient in an open circuit.

Referring now in more detail to the drawings, a patient is illustrated at 10 having a continuous flow peritoneal dialysis catheter 12 implanted in the peritoneal membrane 14 of the patient. Schematically, the implanted catheter is connected by suitable tubing at 16 and 18 which is then, in turn, connected to the continuous flow peritoneal dialysis system which includes a fluid supply A and a fluid delivery control system B of the present invention. The fluid delivery control system includes a single-pass circuit through the peritoneal cavity of the patient.

Referring now to the fluid supply system A of the present invention, a particle filter 20 is included to which a flow of tap water is directed. Water passing through the particle filter next goes to a reverse osmosis unit 22. From the reverse osmosis unit the water flows through a carbon filter 24 which takes out the chloromine in the water. From the carbon filter 24 the water flows into a conventional proportioning machine 26 which takes a 34:1 concentrate solution of non-sterile glucose and electrolytes from supply 27 and mixes it with a proper amount of the purified water coming from the carbon filter 24.

The dialysis solution from the proportioning and mixing unit 26 then passes to a micron particle filter 28 which separates out the non-dissolved particulate matter. Quite often the concentrate being mixed in the proportioning and mixing unit 26 includes some non-dissolved particulate matter. The micron filter 28 is preferably a one (1) micron filter which has an opening sufficient to remove the non-dissolved particulate matter. Both the Milipore and Gilman Manufacturing Companies manufacture a suitable micron filter. The system A provides a properly mixed dialysis solution or dialysate which is non-sterile. The non-sterile fluid from the micron filter 28 is delivered to the continuous delivery and control circuit of the present invention shown in system B. At the outset, the non-sterile dialysis solution flows through a bacterial filter 30 which sterilizes the dialysis solution. The bacterial filter 30 is a conventional high volume bacterial filter which removes all the bacteria to provide a sterile dialysis solution. The fluid then flows to a head vessel 32 which provides a gravity feed means for feeding the sterilized dialysis fluid. Mixing unit 26 includes a pump which is sufficient to pump the dialysis fluid into the head vessel.

A by-pass valve 34 is connected to the outflow of the head vessel 32. The by-pass valve 34 provides a means for preventing controlling the fluid level in the vessel and the head vessel from overflowing. In the event that the head vessel begins to overflow or contains excess sterilized fluid coming from the supply system A, the by-pass valve dumps the excess fluid to a storage container 36. It has been found that it is easier to dump the dialysate rather than start and stop the proportioning and mixing unit 26. A level monitor 38 provides a means for sensing the level of the dialysate fluid in the head vessel 32 and controlling valve 34 in response to the fluid level.

Switching means may also be provided responsive to the level monitor 38 to cut off the proportioning and mixing unit 26 in the event that the bypass valve does not operate correctly and the fluid backs up excessively.

An inflow/outflow valve 40 is connected to the by-pass valve 34 for receiving sterile dialysis fluid from the head vessel 32. The by-pass valve 34 delivers dialysis fluid to the directional valve 40 in an amount depending on the degree to which fluid is being by-passed to the drain tank 36. The by-pass valve is controlled in a manner which will be more fully set forth hereinafter to vary the amount which is delivered to the directional valve. The by-pass valve 34 may be a throttling valve so that it has infinite variability for by-passing fluid from the line to the directional valve 40.

An inflow line 42 (tubing 16) is connected to the directional valve 40 and to an inflow catheter 44 of the double peritoneal catheter 12. The dialysis fluid leaves the peritoneal cavity 14 through an outflow catheter 46 by was of an outflow line 48 which is controlled by and goes through the directional valve 40. There is a pressure monitoring means 50 connected in the outflow line 48 (tubing 18) for sensing the pressure of the fluid in the line and in the peritoneal cavity. The pressure monitor 50 controls the directional valve 40 to maintain a predetermined pressure or pressure range in the peritoneal cavity such that the membrane is properly distended at all times. For this purpose, the directional valve 40 is preferably a double flow valve to provide flows into the catheter and out of the catheter depending on the sensing of pressure 50. A separate inflow line and outflow line must be maintained through the valve 40 to insure sterilization of the inflowing dialysis fluid. A modified single needle hemodialysis control valve manufactured by Vernitron Corporation is suitable. The modified valve is shown schematically in FIG. 2 including an inflow passage 42a and outflow passage 48a controlled by a displaceable needle valve 43 which can be moved to partially or fully occlude either passage in response to abdominal pressure. Normally such a valve is pressure controlled but has only a single outlet line.

In the case where there is excessive pressure in the peritoneal cavity 14 causing the membrane to be overly distended and excessive force exerted on the abdominal contents causing discomfort to the patient, the pressure monitor 50 will send a signal (electrical or mechanical) to the valve 40 to stop the inflow of the dialysis fluid while. maintaining an outflow of the dialysis fluid so that the pressure is relieved. In this case, in the preferred embodiment, needle 43 will occlude the inflow passage 42a, completely in lieu of throttling, and outflow passage 48a remains open to relieve pressure. If the pressure should drop from that normally desired in the cavity, causing underdistention of the membrane and forming of convolutions in which the dialysis fluid may hide thus decreasing the efficiency of the dialysis process, the outflow of dialsyis fluid will be cut off by moving needle valve 43 proportionately to occlude passage 48a and the inflow will be continued so that the pressure is increased as desired. In either case, once the pressure is brought back to a desired value, the inflow and outflow of the dialysis fluid will be brought back to being equal. The pressure range which is normally desired in the abdominal cavity during dialysis is about 150 to 250 cm/water. Any conventional commercially available pressure monitor operable in this range is suitable for sensor 50. The control of valve 40 in response to pressure may be had by any suitable means as is well within the purview of one skilled in the art. For example, electrical control may be had with a single integrated circuit receiving the pressure signals and electrically controlling valve 43.

A flow monitor 54 is inserted in an outflow line 52 which goes from the directional valve 40 to the drain tank 36. The flow monitor 54 monitors the outflow and adjusts the flow through the by-pass valve 34 to the directional valve 40 so that the inflow provided by the by-pass valve 34 to the directional valve 40, is the same as the outflow from the peritoneal catheter. When the directional valve 40 is in its normal setting, with the needle valve 43 in its neutral position, any change in the amount by-passed to disposal 36 by valve 34 as controlled by monitor 54 will directly influence the amount delivered through inflow passage 42a. Hence, should the outflow drop, for example, valve 34 is opened to by-pass more fluid and hence deliver less to valve 40 thus matching the inflow to the decreased outflow. At the same time, pressure monitor 50 keeps check on the pressure inside the peritoneal cavity. Flow monitor 54 may be any suitable sensor such as an ultrasonic flow monitor which is conventionally used.

The valve 40, as controlled by pressure monitor 50, and the valve 34, as controlled by flow monitor 54, provide flow control means for insuring the proper volume and pressure of dialysis fluid in the peritoneal cavity. Normally, valve element 43 will be in its neutral position and the flow monitor acts as a means to controlling the inflow in response to outflow by diverting fluid through valve 34 instead of through valve 40. However, if in so regulating the inflow to equal outflow, the above pressure limits are exceeded, monitor 50 relieves such by controlling valve 40 as described above. Head vessel monitor 38 is independent of the pressure and flow regulating system.

Directional valve 40 could also be a throttling valve instead of an on/off valve. In this case, control of by-pass valve 34 may not be necessary.

The inflow line 42 and outflow line 48 are connected to the inflow catheter 44 and outflow catheter 46 by conventional means. This connection is made at the beginning of dialysis and disconnected at the end in a conventional manner.

A drain pump 56 drains the dialysis fluid in the drain storage container 36 whenever a high level is reached. The fluid is drained into a drain 58 where it is drained away. For this purpose, there is a fluid level detector 60 provided which controls the operation of the pump 56. The aforedescribed drain apparatus provides a disposal means for the dialysis fluid which completes the open, single-pass circuit.

The pressure monitor 50 provides a means for sensing the pressure in the abdomen of the patient. The abdomen has a particular pressure, for example at two liters, that's comfortable. If, for example, one liter is accumulated in the abdominal area, the inner abdominal area is caused to expand by fifty percent and this results in a large degree of discomfort to the patient. In the event the patient becomes overdistended, the pressure monitor will sense a decrease in pressure. In this event, the pressure monitor will control valve 40 which allows additional fluid to enter the cavity to bring the pressure back up to normal. In the event that the cavity becomes underdistended, the pressure will increase and the pressure monitor will sense this increase in pressure to cause the fluid to cut down the inflow and let the outflow of fluid continue until the pressure has stabilized.

Thus it can be seen that a highly advantageous system and method for continuous flow peritoneal dialysis can be had according to the present invention where a single-open circuit.is provided through the patient's peritoneal cavity. A sterilized peritoneal dialysis fluid is provided which is delivered through the cavity in such a manner that the volume and pressure of the fluid are controlled so that proper distention of the membrane occurs for patient comfort and dialysis efficiency. The high rate of fluid flow through the peritoneal cavity is advantageous in that the high rate of circulation increases dialysis efficiency.

Pumping, and its inherent problems, through the cavity is eliminated by a gravity feed system and a drainage tank. By providing a single pass circuit, no recirculation of the dialysis fluid through the membrane occurs reducing any likelihood of residual toxins being recirculated through the peritoneal cavity. By monitoring the outflow of the dialysis fluid from the peritoneal cavity and pressure therein, the membrane is spread out in its efficient condition during dialysis and that no pockets or other hiding places for fluid are provided to cut down on the efficiency of the dialysis process.

It is understood that the line from the bacterial filter 30 to the head vessel 32 will be a disposable presterilized line of tubing. The head vessel 32 will be provided with a sterilized liner which is disposable and connected to presterilized tubing which connects the interior of the liner to the by-pass valve 34. In practice, the by-pass valve 34 will have three legs of disposable tubing in a Y-shape. The lower Y-leg of the disposable valve will be connected to the disposal tank 36. The actuator of the valve 34 will be external of the sterilized valve passages and will act upon the Y-leg of the valve passages leading to disposal tank 36 to occlude the passage more or less in order to divert more or less fluid from the inflow/outflow valve 40. The inflow/outflow valve 40 will be a unit where the valve element 43 is external of tubing which passes through the passages 42a and 48a. The fluid passing through the tubing goes through the valve passages out of contact with any part of the valve so that the valve never has to be sterilized itself. Likewise, the tubing going through the valve passage 42a and connected to the inflow catheter 44 will be disposable. The tubing 48 coming from the outflow catheter 46 and through the outflow passage 48a will likewise be presterilized and disposable as well as the outflow line 52. The pressure monitor 50 will preferably be designed to accept a length of presterilized tubing and sense the pressure of the fluid in the tubing without actually making contact with the fluid so that the pressure monitor may be interchanged with disposable tubing. The flow monitor 54 being of an ultrasonic type flow monitor likewise accepts a length of tubing through the flow monitor and will not ever contact the fluid. In practice, the entire set of tubing from the bacterial filter 30, through the head vessel 32, and including its liner, the tubing from head vessel 32 to valve 34 and including its "Y" tubing passages, and the remainder of the tubing passing through valve 40, and to catheter 12 will be a preformed preglued and presterilized unit. A separate preformed, presterilized and preconnected section of disposable tubing will include the tubing connected to the outflow catheter 46 passing through the flow monitor 50, the outflow passage 48a of valve 40, and the flow monitor 54, and adapted with a terminal connector which may be connected in the disposal tank 36. This will avoid the expense and time of cleaning and sterilizing valves, monitors, and fittings.

Figure 2:
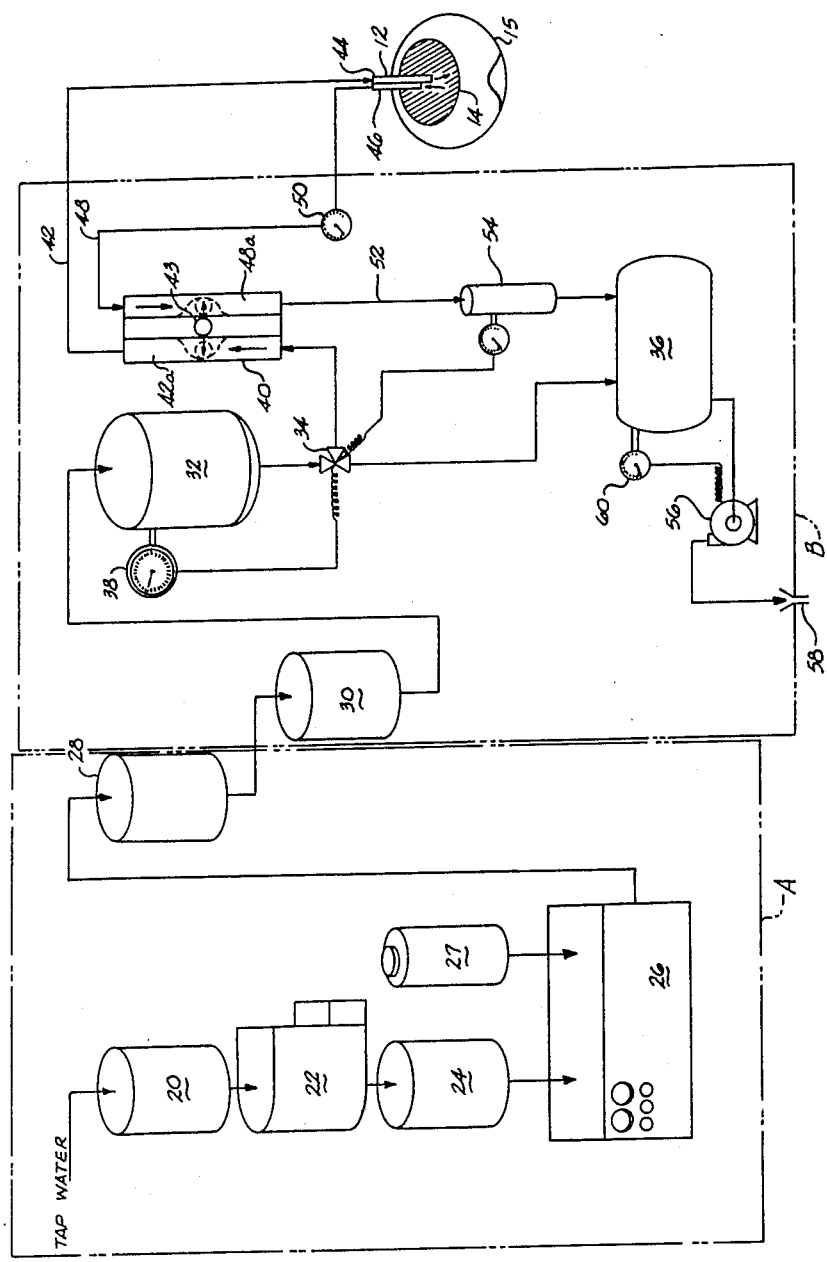
FIG. 2 is a schematic view illustrating a continuous flow peritoneal dialysis system and method according to the present invention.
Figure 3:
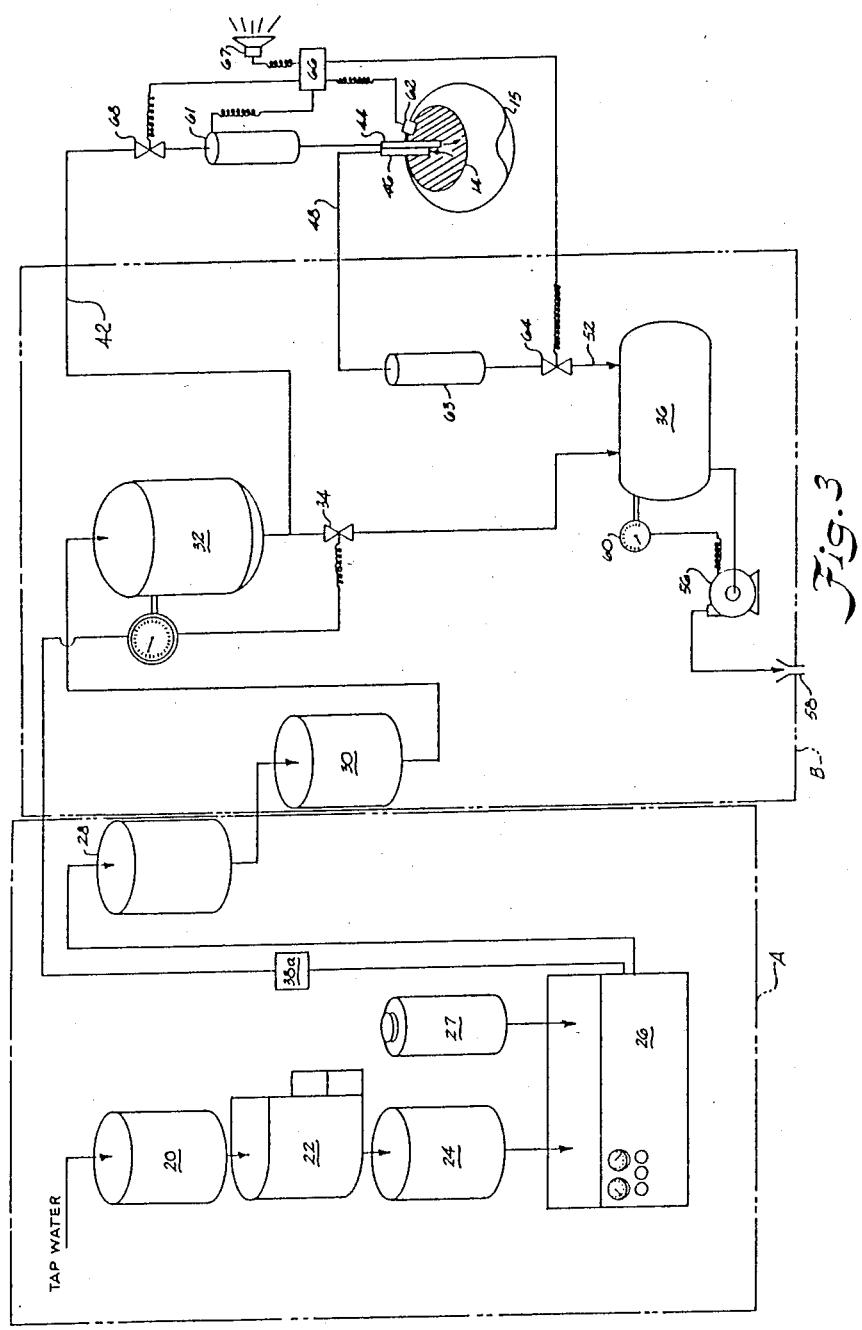
FIG. 3 illustrates an alternate embodiment of the invention wherein means for maintaining a prescribed volume of fluid in the peritoneal cavity is provided by fluid volume monitors, rather than fluid pressure monitors as illustrated in FIG. 2.

FIG. 3 illustrates an alternate embodiment of the invention wherein means for maintaining a prescribed volume of fluid in the peritoneal cavity is provided by fluid volume monitors, rather than fluid pressure monitors as illustrated in FIG. 2, which sense a function of the volume of fluid in the cavity and controlling volume as in accordance with differential flow in and out of the cavity.

In the process and system of FIG. 3, there is an ultrasonic flow monitor 61 disposed in infeed line 42 for monitoring the flow of fluid inflow catheter 44. A second ultrasonic flow monitor 63 is disposed in outflow line 48 connected to outflow catheter 46. Outflow drainline 52 flows from flow monitor 63 to drain tank 36. There is a conventional two-way flow control valve 64 connected in the outflow drainline 52. A second conventional control valve 68 is disposed in infeed line 42 upstream of flow monitor 61. Monitors 61 and 63 thus sense a function of the volume of fluid in the cavity.

Control valve 64 and 68 may be controlled by any suitable process controller 66 in a conventional manner as is well within the skill of one in the art. There is an ultrasonic sensor 62 for sensing the level of fluid and hence the distension of the peritoneal cavity 14. Sensor 62 provides a second means for monitoring fluid volume, in particular dangerous levels of fluid volume. There is an alarm 67 connected to controller 66. In the event that the volume of fluid level should increase to the dangerous amount, an audible alarm is emitted.

In use according to the method and process of the invention, flow monitor 61 senses the amount of fluid flowing into peritoneal cavity 14, and outflow monitor 63 senses the amount of outflow fluid leaving peritoneal cavity 14. These amounts are fed to controller 66. Controller 66 compares the amounts of fluid flowing in the respective flow monitors to control valves 64, 68 and maintains a prescribed volume of fluid in the peritoneal cavity during dialysis. The prescribed amount, of course, can be varied in a conventional manner by input to the controller. The prescribed volume of fluid maintained in peritoneal cavity 14 keeps the peritoneal cavity properly distended during dialysis. If the difference in flow between flow monitor 61 and 63 indicates that the volume of fluid in peritoneal cavity 14 is below the prescribed amount, valve 64 will be closed. If the difference in volumetric flows between flow monitors 61 and 63 indicates that too much fluid is being delivered to peritoneal cavity 14, valve 68 will be cut off. It is also possible that throttling valves may be utilized at 68 and 64 to control the flow in a more continuous manner.

An ultrasonic level monitor 62 is disposed appropriately in the peritoneal cavity 14. If the volume of fluid in peritoneal cavity 14 should drop below the prescribed volume as sensed by monitor 62, controller 66 closes off valve 64 to build up the volume of fluid in peritoneal cavity 14. If ultrasonic monitor 62 senses too large an amount of dialysis fluid in peritoneal cavity 14, alarm circuit 67 is triggered to produce an audible alarm and valve 68 is closed to prevent any further fluid delivery. In the modified embodiment described above, head vessel monitor 38 operates as described previously to control valve 34 in a manner that the level of fluid maintained in vessel 32 is maintained at a desired level.

It will be understood, of course, that while the form of the invention herein shown and described constitutes a preferred embodiment of the invention, it is not intended to illustrate all possible forms of the invention. It will also be understood that the words used are words of description rather than of limitation and that various changes may be made without departing from the spirit and scope of the invention herein disclosed.

What is claimed is:

1. A continuous flow peritoneal dialysis process comprising:
   providing a supply of dialysis fluid;
   sterilizing said dialysis fluid;
   delivering said dialysis fluid to a head vessel;
   providing an inflow and outflow line for connnection to a double catheter having an inflow and outflow catheter implanted in the peritoneal cavity of a patient through which said dialysis fluid continuously flows;
   delivering a flow of sterilized dialysis fluid from said head vessel to said inflow line;
   monitoring a function of the volume of said sterile dialysis fluid in said peritoneal cavity and simultaneously controlling the inflow and outflow of said sterilized dialysis fluid respectively in said inflow and outflow lines so that a desired volume is maintained in said cavity in a manner that proper distension of said cavity is maintained during dialysis; and
   delivering said outflow of sterilized dialysis fluid to a disposal means so that a single pass open circuit for the continuous flow of dialysis fluid is provided through the peritoneal cavity of said patient.

2. The process of claim 1 including providing an inflow valve in said inflow line and an outflow valve in said outflow line for controlling said inflow and outflow of said dialysis fluid from said peritoneal cavity; and providing a flow monitor in each said inflow and outflow line for controlling said inflow and outflow to maintain said desired volume of dialysis fluid in said cavity.

3. The process of claim 1 including monitoring the amount of said dialysis fluid in said peritoneal cavity and controlling said inflow and outflow valves in response thereto to avoid over distension of said cavity.

4. A continuous flow peritoneal dialysis system comprising:

a source of sterile dialysis fluid;

an inflow line adapted for connection to an inflow catheter of a double peritoneal catheter implanted in the peritoneal cavity of a patient;

an outflow line adapted for connection to an outflow catheter of said double peritoneal catheter;

valve means for simultaneously controlling the continuous flow of dialysis fluid in said inflow and outflow lines to thereby control the volume of dialysis fluid in said peritoneal cavity;

disposal means connected to said valve means for disposing of said outflow of dialysis fluid;

volumetric flow monitoring means in the outflow and inflow lines for sensing the flow continuous of dialysis fluid into and out of said peritoneal cavity; and control means controlling said valve means in response to said volumetric flow monitoring means so that flow of said dialysis fluid through said peritoneal cavity is controlled in a manner that a desired volume of fluid is maintained in said cavity for proper distension of said peritoneal cavity during dialysis.

5. The system of claim 4 including:

said means for delivering said dialysis fluid includes a head vessel in which said sterilized dialysis fluid is stored;

a bypass valve connected between said head vessel and said valve means;

a drain line connecting said bypass valve to a disposal means; and flow level sensing means communicating with an interior of said head vessel and controlling said bypass valve to bypass said dialysis fluid from said head vessel to said disposal means should the level of said dialysis fluid reach a predetermined height in said head vessel.

6. The system of claim 4 including fluid level sensing means for sensing the amount of dialysis fluid in said cavity and producing an alarm signal in the event overfilling and overdistension of said cavity occurs.

7. A continuous flow process for peritoneal dialysis wherein a double flow catheter is implanted into the peritoneal cavity of a patient, said catheter having an inflow and outflow catheter for delivering a dialysis fluid into and out of said peritoneal cavity, said process comprising:

providing a supply of sterilized dialysis fluid;

feeding a continuous flow of said dialysis fluid to the inflow catheter of said peritoneal catheter;

simultaneously controlling the continuous inflow and outflow of said sterile dialysis fluid through said peritoneal catheter so that a prescribed volume of said sterile dialysis is maintained in said cavity during dialysis for proper cavity distension; and delivering the outflow of said sterile dialysis fluid from said peritoneal catheter to a disposal means whereby an open single-pass continuous open circuit for said sterile dialysis fluid is provided through said cavity.

8. The process of claim 7 including feeding said sterile dialysis fluid to said peritoneal catheter by means of a gravity feed system without mechanical pumping.

9. The process of claim 8 including storing said dialysis fluid in a head vessel for feeding to said peritoneal catheter and controlling the level of fluid in said head vessel by bypassing a selected amount to said disposal means without going through said peritoneal catheter.

10. The process of claim 7 including monitoring the amount of dialysis fluid in said peritoneal cavity by a second monitor to prevent a dangerous state of distension from occurring.

11. The process of claim 8 including storing said dialysis fluid in a head vessel for monitoring the level of said dialysis fluid in said head vessel, and controlling the delivery of fluid supplied to said head vessel in response to said level of said fluid monitored in said head vessel.

* * * * *